United States Patent [19]

Richardson

[11] 4,332,555
[45] Jun. 1, 1982

[54] DENTAL DRILL CONTROL MECHANISM

[75] Inventor: Howard M. Richardson, Philadelphia, Pa.

[73] Assignee: Dentrex Manufacturing Company, Philadelphia, Pa.

[21] Appl. No.: 221,961

[22] Filed: Jan. 2, 1981

[51] Int. Cl.³ .............................................. A61C 1/02
[52] U.S. Cl. ........................................ 433/28; 433/98
[58] Field of Search ..................... 433/77, 27, 28, 101, 433/98, 79; 251/5 R

[56] References Cited

U.S. PATENT DOCUMENTS

| | | | |
|---|---|---|---|
| 3,691,634 | 9/1972 | Buchtel et al. | 433/79 |
| 3,755,899 | 9/1973 | Betush | 433/28 |
| 3,991,473 | 11/1976 | Morgan | 433/28 |
| 4,069,587 | 11/1978 | Peralta | 433/28 |
| 4,117,861 | 10/1978 | Betush | 433/28 |
| 4,256,130 | 3/1981 | Smith et al. | 251/5 |

*Primary Examiner*—Robert Peshock
*Attorney, Agent, or Firm*—John W. Logan, Jr.

[57] ABSTRACT

A multiple dental handpiece control system is disclosed including a separate control valve block for each handpiece with multiple air and water passages through the valve block. A flexible sleeve is provided surrounding each fluid passage which, when pressure is supplied to its exterior, will collapse about a central fitting in each passage preventing flow from inlet to outlet openings in the central fitting. Pressure in the chamber surrounding the flexible sleeve is relieved when the dental handpiece is removed from its holder and is restored when the handpiece is returned to its holder.

16 Claims, 6 Drawing Figures

DENTAL DRILL CONTROL MECHANISM

DESCRIPTION

1. Technical Field

The present invention relates, in general, to dental equipment and, in particular, to a dental drill operating mechanism and a valve especially usable in such a mechanism.

2. Background Art

Typically, dental drills, in use today, are driven by air turbines. Many are arranged to deliver a water mist to the tooth being drilled to provide a cooling effect. The water mist is developed by combining a stream of water with a supply of air derived from the main air supply which drives the turbine.

Various arrangements of dental drills are available which automatically permit the drill cutting tool to turn and the water mist to be developed when the drill is removed from the drill holder and automatically prevent the drill cutting tool from turning and the water mist from being developed when the drill is inserted in the drill holder. In general, equipment of this type, which is in use today, is unduly complex in construction and expensive to fabricate.

DISCLOSURE OF INVENTION

Accordingly, it is an objective of the present invention to provide a new and improved dental drill operating mechanism.

It is another objective of the present invention to provide a dental drill operating mechanism which is relatively simple in construction and inexpensive to fabricate.

It is a further objective of the present invention to provide a new and improved valve particularly suited for use in a dental drill operating mechanism.

It is yet another objective of the present invention to provide such a valve which is relatively simple in construction and inexpensive to fabricate.

A dental drill operating mechanism, constructed in accordance with the present invention, includes an air source, a water source, and a main valve connected to the air source and the water source for selectively passing air and water to a dental drill. Included within the main valve are control means for controlling the passage of air and water through the valve. The dental drill operating mechanism also includes a control branch connected between the air source and the control means of the main valve. The control branch serves to supply air to the control means to close the main valve and prevent the passage of air and water through the main valve. Also included in the dental drill operating mechanism is an instrument holder for holding the dental drill. The instrument holder has a control valve connected into the control branch for releasing air in the control branch to the atmosphere when the control valve is open. The control valve is closed when the dental drill is in the instrument holder and open when the drill is removed from the holder.

A valve, constructed in accordance with the present invention, includes a valve body having a main fluid passage and a control fluid passage opening in the main fluid passage. Also included in this valve is an inlet fitting within the main fluid passage and extending across the juncture of the main fluid passage and the control fluid passage. The inlet fitting has an inlet passage and an outlet passage. The inlet passage of the fitting extends between an inlet port and a first opening in the outside surface of the fitting and the outlet passage extends between an outlet port and a second opening in the outside surface of the inlet fitting. The valve further includes a flexible tube surrounding the inlet fitting and defining a fluid passage between the first and second openings in the outside surface of the fitting. The flexible tube extends across the juncture of the main fluid passage and the control fluid passage.

When adapted for use in a dental drill operating mechanism, the valve may be arranged with three main fluid passages. One serves to deliver water to the dental drill and two serve to deliver air to the dental drill, one air supply to drive the drill turbine and the other air supply to mist the cooling water.

BRIEF DESCRIPTION OF THE DRAWING

Referring to the drawing.

BEST MODE OF CARRYING OUT THE INVENTION

Figure 1:
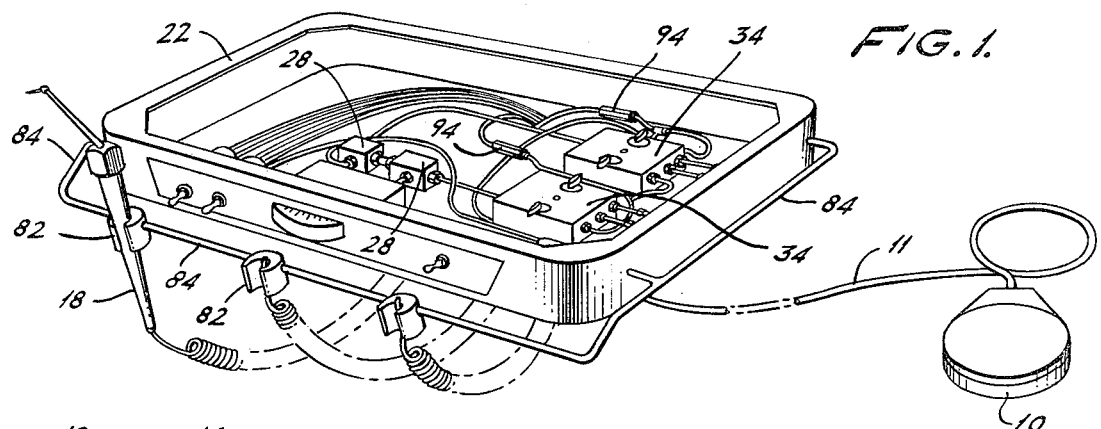
FIG. 1 is a perspective view of a dental drill operating mechanism constructed in accordance with the present invention.
Figure 2:
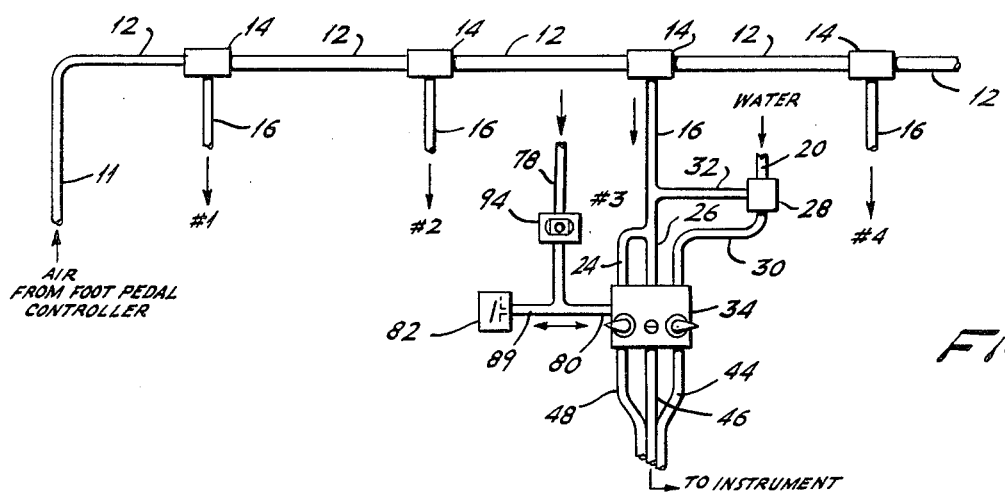
FIG. 2 is a schematic drawing of the FIG. 1 dental drill operating mechanism.

Referring to FIGS. 1 and 2, a dental drill operating mechanism, constructed in accordance with the present invention includes an air source and a water source. The air source may be air supplied under pressure from a conventional foot pedal controller 10 through a hose 11, a manifold 12 and a plurality of junctions 14 to a plurality of air supply lines 16. Each supply line 16 is the source of air for separate dental instruments, such as the dental drill 18 shown in FIG. 1. The water source may be a pipe 20 connected to a domestic water supply. Each water conduit 20 is the source of water for separate dental instruments, such as dental drill 18.

As shown in FIG. 1, dental tray 22 has the facility for supporting a plurality of dental instruments. Three dental instruments are shown but it will be understood that any number may be utilized, depending on the desire of the user. The schematic drawing of FIG. 2 shows the facility for four dental instruments. The piping arrangement for instruments #1, #2 and #4 in FIG. 2 would be the same as illustrated for instrument #3. In particular, air from the air supply line 16 is supplied to air conduits 24 and 26. Water, from water conduit 20, passes through a conventional water control valve 28 to a water conduit 30. The operation of valve 28 is controlled by air pressure from air supply line 16 through a control conduit 32. The arrangement is such that when the foot controller 10 is depressed, air under pressure is supplied through the conduit 32 to valve 28, opening the valve to permit water to flow from the water conduit 20 to the conduit 30. Otherwise, valve 28 is closed to prevent the passage of water to the conduit 30.

The dental drill operating mechanism further includes a main control valve 34 connected to the air and water sources for selectively passing air and water to the dental drill 18. One such valve is associated with each dental instrument.

Figure 3:
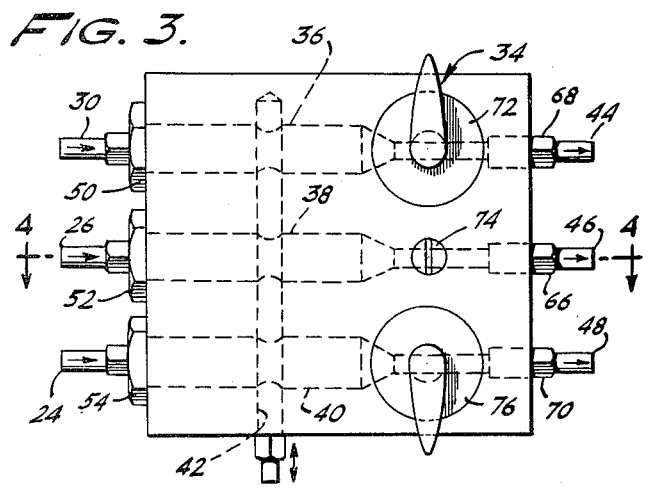
FIG. 3 is a plan view of a valve constructed in accordance with the present invention.
Figure 4:
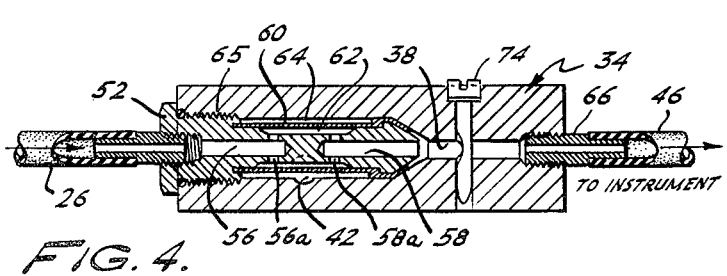
FIG. 4 is a vertical section taken along lines 4—4 of FIG. 3.

FIGS. 3 and 4 show the details of valve 34. This valve, as adapted for use with a dental drill, has three main fluid passages 36, 38 and 40 and a control fluid passage 42 which opens into main fluid passages 36, 38 and 40. For the embodiment of the valve illustrated in the drawings, control fluid passage 42 is disposed perpendicular to main fluid passages 36, 38 and 40. It should be noted that FIG. 4, although a sectional view through main fluid passage 38, also represents sections through main fluid passages 36 and 40, since all three main fluid passages preferably are the same.

Main fluid passage 36 serves to pass water from the water conduit 30 to another water conduit 44. Main fluid passage 38 serves to pass air from the air conduit 26 to another air conduit 46. Main fluid passage 40 serves to pass air from the air conduit 24 to another air conduit 48. Water conduit 44 and air conduits 46 and 48 are connected to the dental instrument, in the usual manner, so that air flowing through conduit 46 drives the air turbine and the water and air in conduits 44 and 48, respectively, are combined to form the cooling water mist.

Main fluid passages 36, 38 and 40 each have an inlet fitting 50, 52 and 54, respectively, which extends across the junctures of control fluid passage 42 and main fluid passages 36, 38 and 40. Fittings 50, 52 and 54 are threadedly secured to valve body 34 and connect conduits 30, 26 and 24 to main fluid passages 36, 38 and 40, respectively. Each inlet fitting has an inlet passage 56 and an outlet passage 58. Inlet passage 56 extends from a fitting for the air conduit 26 toward the midpoint of the fitting 52 and terminates in a radial port 56a. Outlet passage 58 extends from the downstream end of the main fluid passage 38 toward the midpoint of the fitting 52 and terminates in a radial port 58a spaced axially of the fitting from the port 56a. The ports 56a and 58a are at a region of reduced diameter of the fitting 52.

A flexible tube 60 surrounds each of the inlet fittings at the region of reduced diameter to define a fluid passage 62 between the ports 56a and 58a. Specifically, fluid passage 62 is defined by the reduced diameter outside surface of fitting 52 and the inside surface of flexible tube 60.

Inlet fittings 52, 54 and 56 and their associated flexible tubes 60 are arranged to extend across the junctures of control fluid passage 42 and main fluid passages 36, 38 and 40. A chamber 64, defined by the inside surface of the particular main fluid passage and the outside surface of the associated flexible tube, surrounds each flexible tube and control fluid passage 42 extends into each of the chambers 64. Flexible tube 60 is secured in place by crimping inlet fitting 52 after the tube has been slipped into a recess 65 and by wedging the other end of the tube between the inlet fitting and the walls of main fluid passage 38 as the inlet fitting is threaded into valve body 34.

Outlet passage 58 of inlet fitting 52 opens into main fluid passage 38. An outlet fitting 66 is threadedly secured to valve 34 at the outlet of main fluid passage 38 and is connected to air conduit 46. Similar outlet fittings 68 and 70 are threadedly secured to valve 34 at the outlets of main fluid passages 36 and 40, respectively, and are connected to water conduit 44 and air conduit 48, respectively. Each of the main fluid passages has a manually operated control valve 72, 74 and 76 which may be set by the user to control the rate of flow of the individual fluids passing through valve 34.

Control fluid passage 42 serves to control the passage of water and air through main valve 34. Air from the main air supply is supplied to a control conduit 78 and an inlet conduit 80 to the control fluid passage 42. As air pressure increases in the chambers 64, the flexible tubes 60 collapse and close off fluid passages 62 between openings 56a and 58a of the fittings. In this way, water from water conduit 30 and air from air conduits 26 and 24 are prevented from passing to water conduit 44 and air conduits 46 and 48, respectively. Similarly, with a decrease in pressure of air in the control fluid passage 42, flexible tubes 60 are in their relaxed position permitting fluid to pass from inlet passages 56 to outlet passages 58 through fluid passages 62.

Also included in a dental drill operating mechanism, constructed in accordance with the present invention, is an instrument holder 82 for holding dental drill 18. As seen in FIG. 1, more than one instrument holder may be provided on dental tray 22. The instrument holders are secured to a stiff wire railing 84 surrounding a portion of the dental tray 22.

Figure 5:
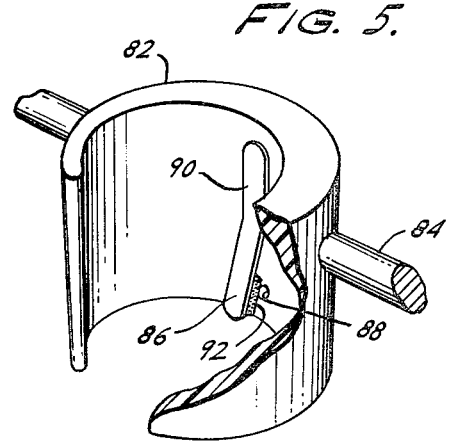
FIG. 5 is a perspective view of an instrument holder usable in the FIG. 1 mechanism.
Figure 6:
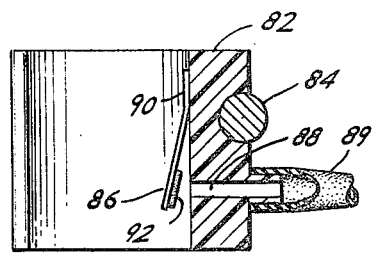
FIG. 6 is a vertical section of the FIG. 5 instrument holder.

FIGS. 5 and 6 show the details of instrument holder 82. The instrument holder has a control valve 86 which is connected through a passage 88 in the wall of the instrument holder and a conduit 89 to the junction of control conduit 78 and inlet conduit 80. Control valve 86 is composed of a leaf spring 90 and a pad 92 which is movable toward and away from passage 88 in the wall of the instrument holder. As dental drill 18 is inserted into instrument holder 82, pad 92 moves into contact with the wall of the instrument holder to close off passage 88. When dental drill 18 is removed from instrument holder 82, pad 92 moves away from the wall of the instrument holder to open passage 88.

Air flow in control conduit 78 passes through a restrictor 94 which limits the rate of flow of air through the control conduit. With dental drill 18 in instrument holder 82, passage 88 in the wall of the instrument holder is closed and air flow through conduit 89 is blocked. Thus, the air flow from restrictor 94 passes through inlet conduit 80 to control fluid passage 42 in main valve 34 and causes flexible tubes 60 to collapse. This prevents fluid from passing through main valve 34. When dental drill 18 is removed from instrument holder 82, passage 88 in the wall of the instrument holder is opened and air flow from restrictor 94 and air in control fluid passage 42 follow the path of least resistance through conduit 89 and passage 88 to the atmosphere. With a decrease in air pressure in the control fluid passage 42, flexible tubes 60 are in their relaxed position and fluid is permitted to pass through main valve 34.

While in the foregoing there has been described a preferred embodiment of the invention, it should be understood to those skilled in the art that various modifications and changes can be made without departing from the true spirit and scope of the invention as recited in the claims.

I claim:

1. A dental drill control mechanism comprising:
   a source of first fluid;
   a source of second fluid;
   means for conveying said first and second fluids from said respective first and second fluid sources to said dental drill;

fluid activated means associated with said conveying means for controlling the passage of said first and second fluids to said dental drill;

means for supplying said first fluid at a reduced pressure directly to said fluid activated controlling means, said fluid presence operating said fluid activated controlling means to close off said first and second fluids to said dental drill; and means for holding said dental drill, including valving means connected to said first fluid reduced pressure supply means for selectively releasing said first fluid supplied from said reduced pressure supply means and from said fluid activated controlling means, said releasing thereby opening said fluid activated controlling means passage of said first and second fluids said dental drill presence in said holding means operating said valving means to cause said first fluid pressure at said fluid activated controlling means.

2. The dental drill control mechanism of claim 1 wherein said reduced pressure supplying means includes a restrictor connected between said first fluid source and said controlling means.

3. The dental drill control mechanism of claim 2 wherein said fluid activated controlling means includes a first passageway having a collapsible portion, said first passageway being connected between one of said fluid sources and said dental drill; and a second passageway surrounding said first passageway collapsible portion, said second passageway being directly connected to said restrictor output.

4. The dental drill control mechanism of claim 3 wherein said first fluid is air and wherein said second fluid is water.

5. The dental drill control mechanism of claim 4 wherein said holding means is a dental drill holder; and wherein said valving means includes an opening to the atmosphere, said opening being connected directly to said restrictor output and said second passageway, a valve member closing off said opening when said dental drill is seated in said holder, said dental drill operating directly on said valve member.

6. The dental drill control mechanism of claim 5 wherein said valve member is a leaf valve; wherein said fluid activated controlling means first passageway is connected to said air source and wherein said fluid activated controlling means includes a third passageway connected to said water source, said third passageway having a collapsible portion, said second passageway also surrounding said third passageway collapsible portion;

wherein said conveying means includes a first supply line connecting said air source to one end of said first passageway, a second supply line connecting the other end of said first passageway to said dental drill, a third supply line connecting said water source to a first end of said third passageway, a fourth supply line connecting the other end of said third passageway to said dental drill, and a fifth supply line connecting said restrictor output to said dental drill holder opening and a first end of said second passageway; and wherein said second passageway other end is closed.

7. In a dental drill operating mechanism, a control valve comprising:

a valve body having a main fluid passageway, said main fluid passageway having a collapsible tubular section thereof; and a control passageway in said valve body, said second passageway intersecting said control passageway collapsible tubular section, said control passageway having rigid walls 8. The valve of claim 7 wherein said main fluid passageway collapsible tubular section passes through said control passageway being completely surrounded by said control passageway rigid walls.

9. The valve of claim 8 wherein said control passageway is closed at one end thereof.

10. The valve of claim 9 wherein said main fluid passageway includes:

an inlet fitting sealingly engaging said valve body at one end of said main fluid passageway having an inlet passageway extending into said valve body;

a first port connecting said inlet passageway to the interior of said collapsible tubular section;

an outlet passageway extending through said valve body in sealing engagement therewith; and a second port connecting said outlet passageway to the interior of said collapsible tubular section.

11. The valve of claim 10 wherein said main fluid passageway also includes a chamber in which said inlet fitting, said inlet passageway, said outlet passageway, said first and second ports, and said collapsible tubular section reside.

12. The valve of claim 11 wherein said chamber has a first threaded end and a second tapered end.

13. The valve of claim 12 wherein said main fluid passageway also includes an outlet fitting containing said outlet passageway.

14. The valve of claim 13 wherein said inlet fitting is threaded and mates with said chamber threaded end; said outlet fitting is tapered and seats against said chamber tapered end; and said collapsible tubular section sealingly connects said inlet fitting to said outlet fitting.

15. The valve of claim 14 wherein control passageway intersects said main fluid passageway perpendicularly through said chamber and beyond.

16. The valve of claim 15 also including means for relieving pressure in said control passageway; said inlet and outlet passageways each extend axially to said chamber and said first and second ports extend radially.

* * * * *